(12) United States Patent
O'Reilly et al.

(10) Patent No.: US 7,799,005 B2
(45) Date of Patent: Sep. 21, 2010

(54) INTRAVAGINAL ARTICLE MEASURING DEVICE

(75) Inventors: Marie Brigid O'Reilly, Cincinnati, OH (US); Jacqueline Ann Daniels, Hamilton, OH (US); John David Norcom, Middletown, OH (US); Mary Alison Jett, Lawrenceburg, IN (US); David Joseph Caracci, Evendale, OH (US); John Richard Noel, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 24 days.

(21) Appl. No.: 11/606,830

(22) Filed: Nov. 30, 2006

(65) Prior Publication Data

US 2008/0132807 A1 Jun. 5, 2008

(51) Int. Cl.
*A61F 13/15* (2006.01)
*A61F 13/20* (2006.01)

(52) U.S. Cl. .................. 604/385.18; 604/904

(58) Field of Classification Search .......... 604/385.17, 604/385.18, 904
See application file for complete search history.

(56) References Cited

U.S. PATENT DOCUMENTS

| | | | |
|---|---|---|---|
| 1,054,802 A * | 3/1913 | Spiro | 600/588 |
| 3,101,714 A | 8/1963 | Penksa | |
| 3,570,489 A | 3/1971 | Brown | |
| 3,794,024 A | 2/1974 | Kokx et al. | |
| 3,815,600 A | 6/1974 | Groves | |
| 4,198,978 A * | 4/1980 | Nigro | 604/14 |
| 4,258,704 A | 3/1981 | Hill | |
| 4,332,251 A | 6/1982 | Thompson | |
| 4,361,150 A | 11/1982 | Voss | |
| 4,942,882 A * | 7/1990 | Bellinson | 600/588 |
| 5,609,586 A | 3/1997 | Zadini et al. | |
| 6,258,075 B1 * | 7/2001 | Taylor et al. | 604/385.18 |
| 6,312,419 B1 * | 11/2001 | Durel-Crain | 604/385.18 |
| 6,348,640 B1 | 2/2002 | Navot et al. | |
| 6,370,912 B1 | 4/2002 | Sutton | |
| 6,418,930 B1 | 7/2002 | Fowler | |
| 6,432,096 B1 | 8/2002 | McFall et al. | |
| 6,554,814 B1 | 4/2003 | Agyapong et al. | |
| 6,596,919 B2 | 7/2003 | Williams | |
| 6,676,625 B2 | 1/2004 | Bernard | |
| 6,740,070 B2 | 5/2004 | Agyapong et al. | |
| 6,904,820 B2 | 6/2005 | Tate et al. | |

(Continued)

OTHER PUBLICATIONS

Miranda A. Farage, Debbie A. Gilpin, Ninah A. Enane and Sue Baldwin, "Development of a new test for mechanical irritation: behind the knee as a test site", Skin Research and Technology 2001; 7: 193-203, ISSN 0909-752X, Printed in Denmark.

(Continued)

*Primary Examiner*—Michele Kidwell
(74) *Attorney, Agent, or Firm*—James E. Oehlenschlager

(57) ABSTRACT

A method is provided for measuring the insertion distance of an intravaginal article within a human vaginal cavity. The method uses a measuring device, which can be slidably attached to a withdrawal means of a vaginally inserted intravaginal article. The measuring device may be moved along the withdrawal means to a predetermined position, and then fixedly secured to the withdrawal means. The intravaginal article is then removed from the vaginal cavity and the insertion distance determined.

17 Claims, 9 Drawing Sheets

U.S. PATENT DOCUMENTS

| | | |
|---|---|---|
| 7,036,511 B2 | 5/2006 | Nissenkorn |
| 7,137,970 B1 | 11/2006 | Farage |
| 2003/0171443 A1 | 9/2003 | Erbacher |
| 2004/0003670 A1 | 8/2004 | Minerath, III et al. |
| 2005/0171463 A1* | 8/2005 | Suga .......................... 604/15 |
| 2005/0273037 A1 | 12/2005 | Osborn, III et al. |
| 2005/0273043 A1 | 12/2005 | Osborn, III et al. |
| 2006/0004319 A1 | 1/2006 | Berg, Jr. et al. |
| 2006/0004320 A1 | 1/2006 | Berg, Jr. et al. |
| 2006/0161096 A1 | 7/2006 | Osborn, III et al. |

OTHER PUBLICATIONS

PCT International Search Report Apr. 23, 2007.

* cited by examiner

INTRAVAGINAL ARTICLE MEASURING DEVICE

FIELD OF THE INVENTION

The disclosed invention relates generally to intravaginal articles, such as tampons and pessaries.

BACKGROUND OF THE INVENTION

Intravaginal articles such as tampons and incontinence devices (pessaries) have long been known in the art. Most commercially available tampons include an absorbent member comprised of an absorbent core, and a withdrawal cord, which is used to aid in the removal of the tampon after use. The absorbent member of a tampon is often compressed to a size sufficient to facilitate insertion into the vaginal cavity. As fluid is absorbed, these compressed tampons re-expand toward their original pre-compressed size, and eventually become large enough to prevent fluid (menses) from leaking out of the vaginal cavity. A pessary is a nonabsorbent or minimally absorbent article, that is insertable into the vaginal cavity, and used to support the uterus, vagina, bladder or rectum. In some instances a pessary can be used to reduce incontinence, for example when used to support the bladder It is known that the position of an intravaginal article within the vaginal cavity can directly influence the intravaginal article's effectiveness. For example, if a tampon is in an improper position within the vaginal cavity, the tampon's ability to reduce and/or eliminate leakage of menses from the vaginal cavity can be compromised. For instance, applicators can place an intravaginal article too low in a body cavity. When a tampon or pessary is placed too low in the vaginal cavity, the too low position can cause bodily discomfort to the user. This discomfort is caused by the pressure exerted from the sphincter muscles of the vagina against the tampon or pessary. In addition, if the tampon or pessary is placed too low within the vaginal cavity, accidental expulsion of the tampon or pessary is a highly undesired risk to the user. Further, improperly placed tampons or pessaries can over time cause increased vaginal discharge, vaginal irritation, ulceration, bleeding and dyspareunia (painful intercourse for the female).

Alternatively, conventional telescoping "push" type applicators can place a tampon too high in the vaginal cavity. The higher the tampon is placed, the greater the chance of menses leaking out of the vaginal cavity, due to the tampon being positioned above the major path of the menstrual flow. Therefore, the failure of the tampon to prevent the leakage of menstrual fluid is not because of a defect in the tampon, but is rather due to the tampon's position within the vaginal cavity. Additionally, current tampon applicators are designed to "push" the tampon out of the outer tube, substantially higher than the insertion end of the outer tube. This often causes the tampon to be deflected by the cervix/anterior fornix, resulting in an off-centered position of the tampon, and menstrual leakage from the vaginal cavity.

One attempt in the prior art to prevent the leakage of menstrual fluid from the vaginal cavity, has been through the use of secondary absorbent members. A secondary absorbent member is used to reduce bypass leakage of menses out of the vaginal cavity, by having the secondary member positioned at or near the vaginal opening. Secondary absorbent members may be integral with the absorbent core of the tampon, and others may be movably attached to the withdrawal means of the tampon.

Movably attached secondary absorbent members, are positioned at the vaginal opening after insertion of the tampon into the vaginal cavity. However, the movably attached secondary absorbent is not fixedly secured to the withdrawal means. As such, the movably attached secondary absorbent member, will often move along the withdrawal means into the vaginal cavity, or may leave the vaginal opening. Further, the movably attached secondary absorbent member will often expand in size due to the absorption of menses and other fluids, causing irritation to vaginal tissue around the vaginal opening.

What is needed in the art is a means to determine the insertion distance of an intravaginal article within a body cavity. Therefore, it would be beneficial to provide a method, which can accurately measure the insertion distance of an intravaginal article within the vaginal cavity.

SUMMARY OF THE INVENTION

A method is provided for determining the insertion distance of an intravaginal article within a vaginal cavity, which comprises the steps of providing an intravaginal article wherein said intravaginal article includes a withdrawal end and a withdrawal means, inserting said intravaginal article into a vaginal cavity, providing a measurement device, slidably attaching said measurement device to said withdrawal means, fixedly securing said measurement device to said withdrawal means, removing said intravaginal article from said vaginal cavity, measuring insertion distance between a portion of said intravaginal article and a portion of said measuring device.

A method is provided for controlling the insertion distance of an intravaginal article within a vaginal cavity, which comprises the steps of providing an intravaginal article wherein said intravaginal article includes a withdrawal means, providing a measurement device, slidably attaching said measurement device to said withdrawal means, fixedly securing said measurement device to said withdrawal means, inserting said intravaginal article into a vaginal cavity, detaching said measurement device from said withdrawal means.

A tampon is provided which comprises an absorbent member having a withdrawal end, and a withdrawal means attached to said absorbent member and extending beyond at least said withdrawal end, wherein a measuring device is slidably attached to said withdrawal means and can be fixedly secured to said withdrawal means.

In certain embodiments the withdrawal means of the tampon may include at least one indicator. Wherein the indicator may be a hash mark, picture, letter, number, color, symbol, or combinations thereof.

BRIEF DESCRIPTION OF THE DRAWINGS

While the specification concludes with claims particularly pointing out and distinctly claiming the invention, it is believed that the invention will be better understood from the following description of embodiments taken in conjunction with the accompanying drawings wherein like designations are used to designate substantially identical elements, and in which:

DETAILED DESCRIPTION OF THE INVENTION

Figure 1:
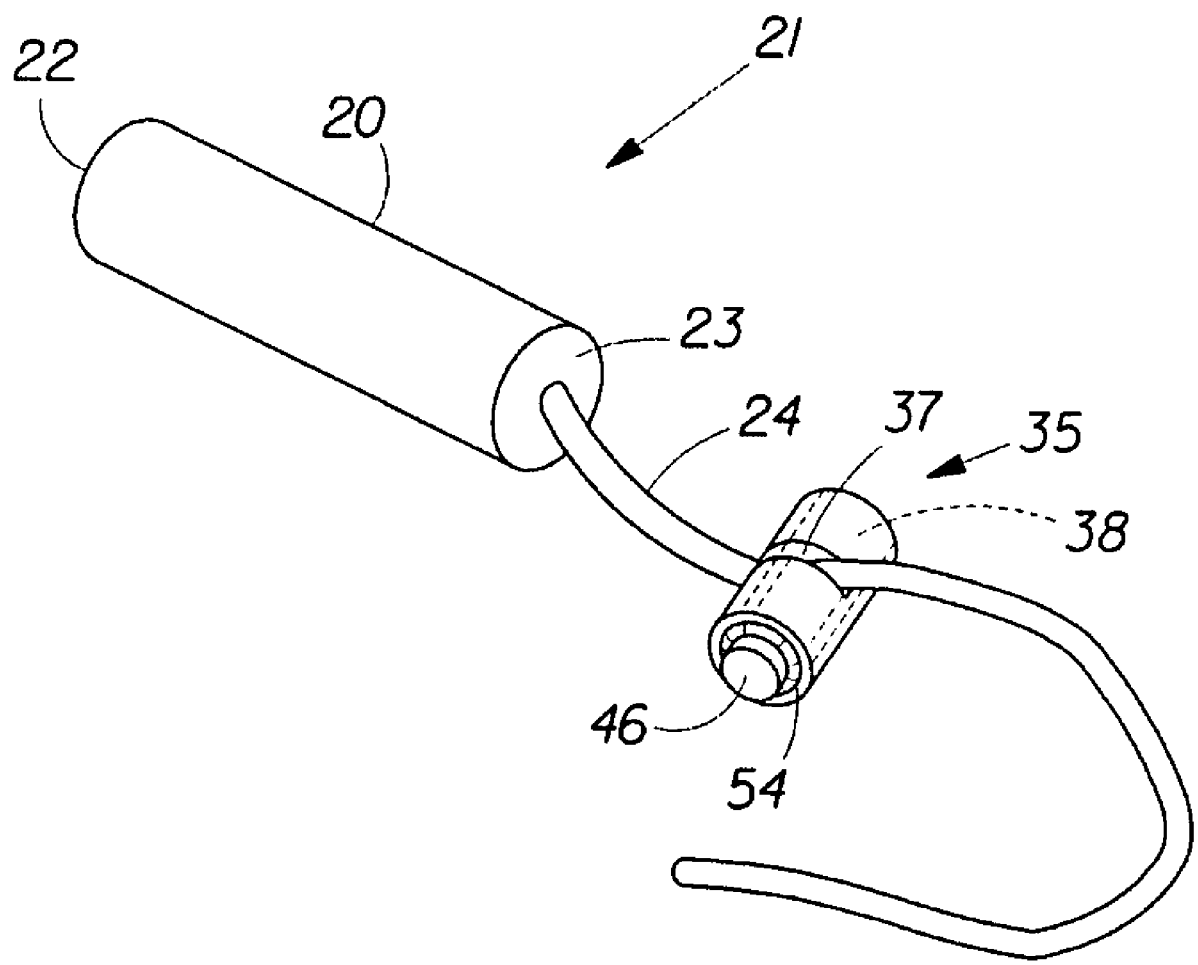
FIG. 1 is a perspective view of an embodiment of a tampon and measuring device of the present invention.

The present invention is directed to a method for measuring the insertion distance of an intravaginal article within a human vaginal cavity. In certain embodiments as shown in FIG. 1 the intravaginal article may be a tampon 21. The tampon 21 has an insertion end 22, a withdrawal end 23, an absorbent member 20 (sometimes also referred to as the "absorbent core"), and a withdrawal means 24. A measuring device 35 comprising a longitudinal passage 38, an attachment section 37, a fastener 46, and a protective ring 54 may be slidably attached and/or fixedly secured to the withdrawal means 24 of the tampon 21.

The term "insertion distance" as used herein, is the distance that an intravaginal article has been inserted into the vaginal cavity, as measured between a portion of the intravaginal article and a portion of a measuring device. For example, the insertion distance could be measured between the withdrawal end of a tampon, and the surface of the measuring device closest to the withdrawal end of the tampon. However, the portion of the intravaginal article and the portion of the measuring device that is being measured should be consistent with regard to multiple measurements taken by individual users and groups of users. The consistency allows the measurements to be compared. As used herein the term "intravaginal article" refers to a tampon or pessary.

When an intravaginal article fails or succeeds, the insertion distance of the intravaginal article within the vaginal cavity can be determined using the method of the present invention. The information regarding the insertion distance at which intravaginal articles succeed or fail, may be utilized to improve the insertion of intravaginal articles into the vaginal cavity. For example, modifications could be made to intravaginal article applicators, and/or improved application instructions can be developed to help ensure that the intravaginal article is placed in a favorable location within the vaginal cavity. The method can also be used to create improved intravaginal articles, by removing the insertion distance of the intravaginal article within the vaginal cavity as a reason for failure. The failure then could be attributed to the design of the intravaginal article, rather than the intravaginal article's insertion distance. This can lead to improvements such as changes in the materials used to produce intravaginal articles, or changes to the size or shape of the intravaginal articles.

Additionally, the method provides consistent reliable results, which can be reproduced with no harm to a user. The measuring device is easily attachable to the withdrawal means of an intravaginal article, without the risk of causing trauma to surrounding tissue. This is a concern, as the vaginal opening is not in direct view of a user.

In accordance with the present invention, the measurement of the insertion distance of an intravaginal article is initiated by the insertion of an intravaginal article into a human vaginal cavity. In certain embodiments the user may be provided with instructions on how to use the intravaginal article and/or measuring device, such as oral, and/or visual instructions, video instructions, or a printed handout. The insertion of the intravaginal article can be done in any position, for example the user may be standing, sitting, or squatting while inserting the intravaginal article.

As stated previously and shown in FIG. 1 the intravaginal article may be a tampon 21, comprising an absorbent member 20. The absorbent member 20 may be compressed into a generally cylindrical configuration. While the absorbent member 20 may be compressed into a substantially cylindrical configuration, other shapes are also possible. These may include shapes having a cross section, which may be described as rectangular, triangular, trapezoidal, semi-circular, elliptical or other suitable shapes.

The absorbent member 20 of the tampon 21 may be constructed from a wide variety of absorbent materials. Such absorbent materials may include but are not limited to synthetic fibers, natural fibers or combinations thereof. The natural fibers may include but are not limited to cotton, wood pulp, flax, hemp and rayon such as GALAXY Rayon (a tri-lobed rayon structure) available as 6140 Rayon; or SARILLE L rayon (a round fiber rayon), both available from Kelheim Fibers of Kelheim, Germany, cotton, wood pulp, flax, and hemp. The synthetic fibers can include but are not limited to fibers such as polyester, polyolefin, nylon, polypropylene, polyethylene, polyacrylic, vinyl polyacetate, polyacrylate, cellulose acetate or bicomponent fibers such as bicomponent polyethylene and polypropylene fibers. Additional absorbent material include materials, such as peat moss, absorbent foams (such as those disclosed in U.S. Pat. No. 3,994,298 issued to DesMarais on Nov. 30, 1976, U.S. Pat. No. 5,795,921 issued to Dyer, et. al both incorporated by reference herein,) capillary channel fibers (such as those disclosed in U.S. Pat. No. 5,356,405 issued to Thompson, et. al incorporated by reference herein), high capacity fibers (such as those disclosed in U.S. Pat. No. 4,044,766 issued Kaczmarzk et al. Aug. 30, 1977 incorporated by reference herein), superabsorbent polymers or absorbent gelling materials (such as those disclosed in U.S. Pat. No. 5,830,543 issued to Miyake, et al incorporated by reference herein) may be incorporated into the tampon.

Withdrawal means 24 can be a string or cord and, may be made of any suitable material known in the prior art, such as cotton and polyester. In addition, the withdrawal means 24 may be in the form of a ribbon, loop, or the like. The withdrawal means 24, shown in FIG. 1, may be joined to any suitable location on the tampon 21 for removal of the tampon 21 after use. The withdrawal means 24 may be joined to the absorbent member 20 and extend beyond at least the withdrawal end 23 of the absorbent member 20. The withdrawal means 24 may be integral with, or an extension of another element of the tampon 21, such as an overwrap (not shown). Additionally, the withdrawal means 24 may be integral with a mass of secondary absorbent material (not shown). The withdrawal means 24 may be attached in any suitable manner known in the art including sewing, adhesive attachment, or a combination of known bonding methods. The tampon 21 of the present invention may also be provided with more than one withdrawal means 24.

In certain embodiments the intravaginal article may be a pessary (not shown). The pessary may be a non absorbent or minimally absorbent vaginal insert. The pessary may be used for reducing urine leakage, rectal support or uterine support. The pessary may have a withdrawal means. Pessaries may have any variety of sizes and shapes such as cylinders, ovate, spherical, tubular, annual rings, "U" shaped, cup shaped, rings, cubes or donut shaped. Pessaries function by direct application of support, which may be produced by expansion of a pessary by selection of material or by inflation of the device. Pessaries may be made of any material that is not harmful to human use, such as materials that are biocompatible, hypoallergenic or easily cleaned. For example, the materials may be selected from silicones or plastics such as polyethylene, polypropylene, polyester, polyurethane, poly(vinyl chloride), polyisobutylene, polychloroprene, polystyrene and polybutadiene.

The intravaginal articles of the present invention may be inserted digitally or with the use of an applicator. Any of the currently available applicators may be used for insertion of an intravaginal article. Such applicators are typically of a "tube and plunger" type arrangement and may be plastic, paper, or any other suitable material. Additionally, a "compact" type applicator may be used.

In certain embodiments the user of an intravaginal article determines when the intravaginal article is removed from the vaginal cavity. The removal of the intravaginal article may be immediately or soon after insertion into the vaginal cavity. The user may also remove the intravaginal article after the intravaginal article's normal course of use, for example, when the use of the intravaginal article becomes uncomfortable, or in the case of a tampon when the tampon becomes saturated, or needs to be removed overnight. In certain embodiments the user may record the length of time (insertion to removal) the intravaginal article was in the vaginal cavity, and the reason for removal. The user may make such records in a written log.

Prior to removal of the intravaginal article the measuring device 35 may be slidably attached to the withdrawal means 24 of an intravaginal article such as a tampon 21 as shown in FIG. 1 In certain embodiments, the measuring device 35 can be cylindrical, ovoid, or spherical. In certain embodiments, the measuring device 35 may have a length of about 3 cm and a width of about 1 cm. In certain other embodiments, the measuring device 35 may have a length of about 2.5 cm and a width of about 1.25 cm. The measuring device 35 may be fabricated from any substantially non-absorbent material, for example wood, glass, metal, plastic, such as molded acetal polymers, or composite materials containing combinations thereof. It should be understood that while a tampon 21 is used to illustrate embodiments off the invention, that a pessary may also be used in any embodiment described herein. The measuring device 35 may be slidably attached to the withdrawal means 24 of a tampon 21 anywhere along the length of the withdrawal means 24. In certain embodiments, to slidably attach the measuring device 35 one hand of the user grasps the withdrawal means 24 and the other hand slidably attaches the measuring device 35 to the withdrawal means 24. The measuring device 35 is "slidably attached" to the withdrawal means 24, in that the measuring device 35 can be freely moved along the length of the withdrawal means 24. Additionally, the measuring device 35 may be removed from the withdrawal means 24, at anytime during the measuring device's 35 movement along the length of the withdrawal means 24.

Figure 2:
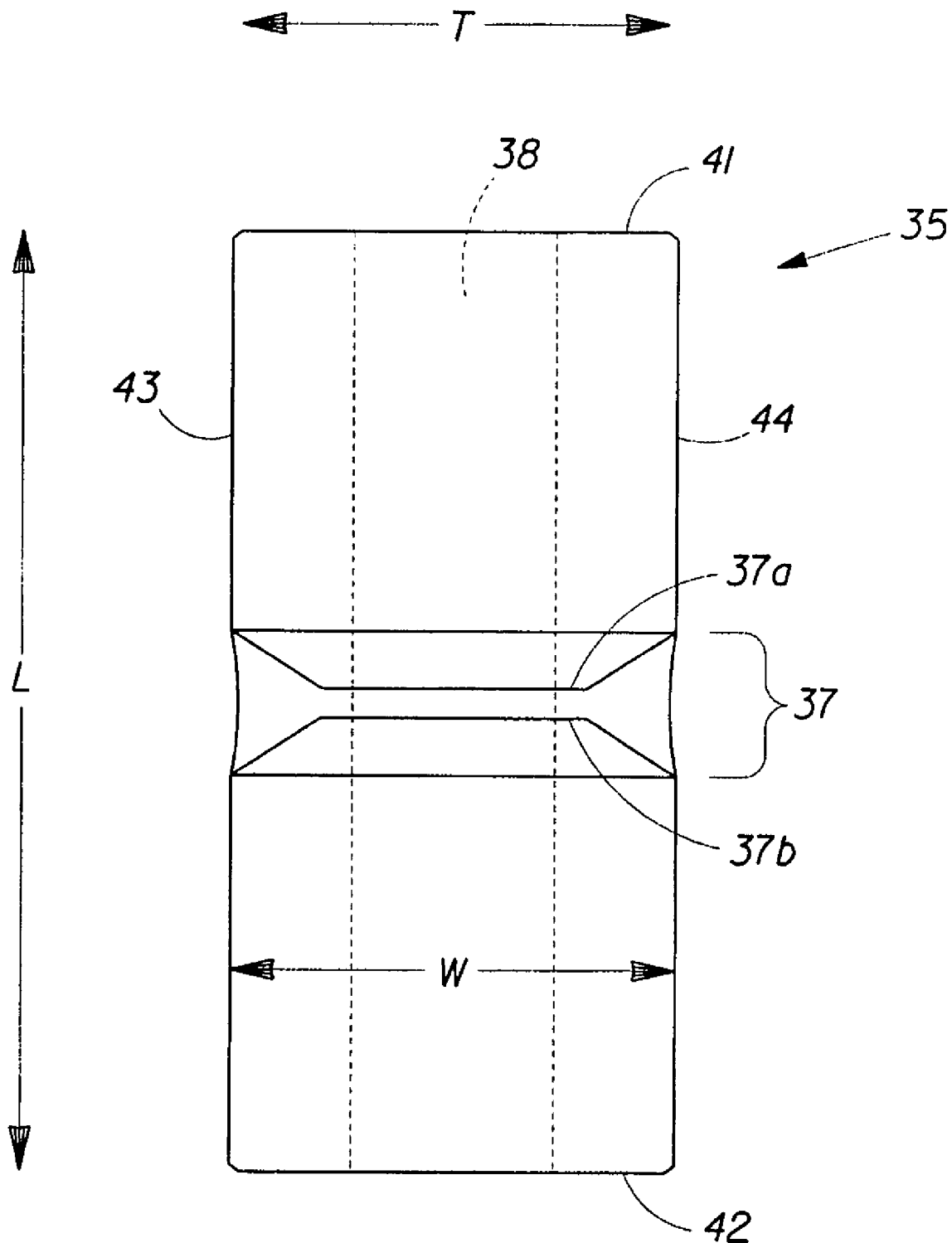
FIG. 2 is a frontal view of an embodiment of a measuring device of the present invention.

In certain embodiments as shown in FIG. 1, the measuring device 35 may be slidably attached to the withdrawal means 24 through the use of an attachment section 37. FIG. 2 is a further detailed view of the measuring device 35 of FIG. 1, wherein for the sake of clarity the fastener 46 and protective ring 54 are not shown. As shown in FIG. 2 the measuring device 35 has a longitudinal axis "L" and a transverse axis "T" which is perpendicular in direction to the longitudinal axis. The attachment section 37 has a width "w" and may be a notch or slot perpendicular to the longitudinal axis of the measuring device 35. In certain embodiments, the width of the attachment section 37 bisects the measuring device 35 from one side 43 of the measuring device 35 to the other side 44 as shown in FIG. 2. The attachment section 37 may be located anywhere along the longitudinal length of the measuring device 35 between the first end 41 and the second end 42. The attachment section may have a first side 37a and a second side 37b. In certain embodiments the distance between the first side 37a and the second side 37b of the attachment section 37, is less than the width of the withdrawal means 24, to which the measuring device 35 will be slidably attached. In certain embodiments the distance between the first side 37a and the second side 37b of the attachment section 37 will be about 0.1 mm to about 5 mm, in certain other embodiments the distance between the first side 37a and the second side 37b of the attachment section 37 will be about 0.5 mm to about 3 mm. The distance between the first side 37a and second side 37b, may vary along the width of the attachment section 37. The first side 37a and second side 37b of the attachment section, may be any shape along the width of the attachment section 37, such as angled or curved.

Figure 3:
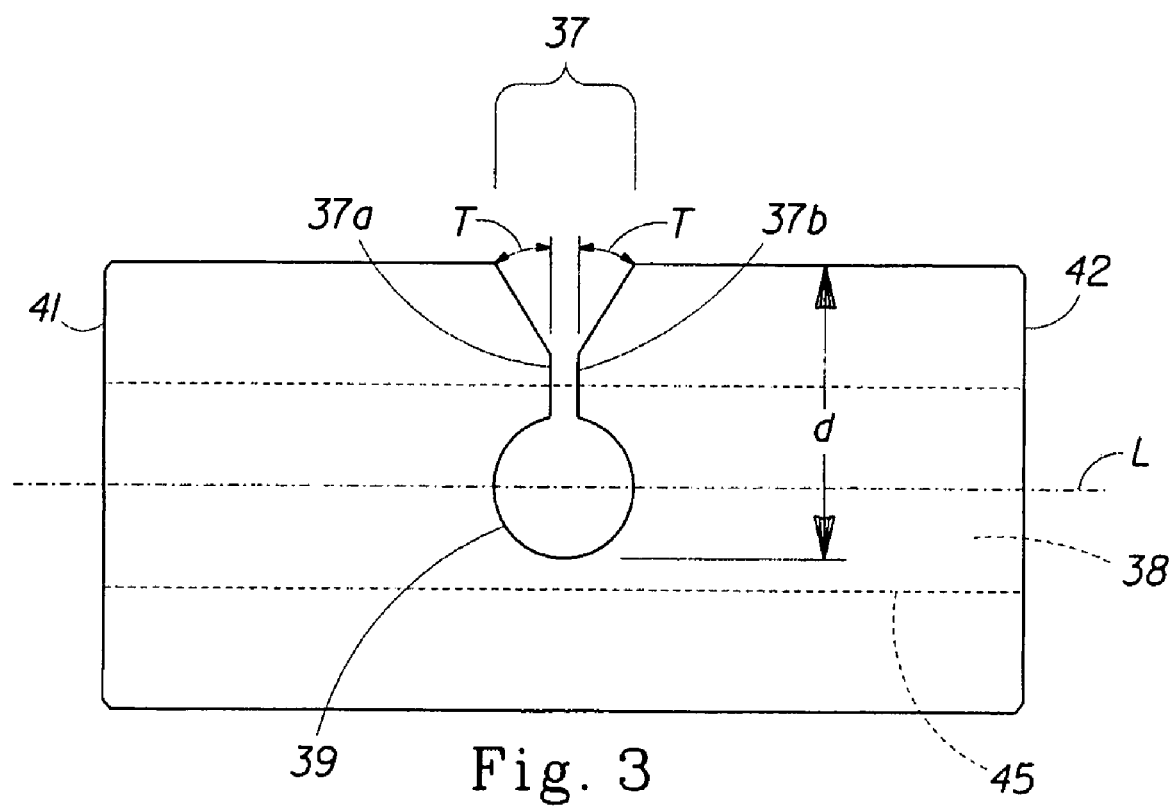
FIG. 3 is a side view of the measuring device of FIG. 2.
Figure 4:
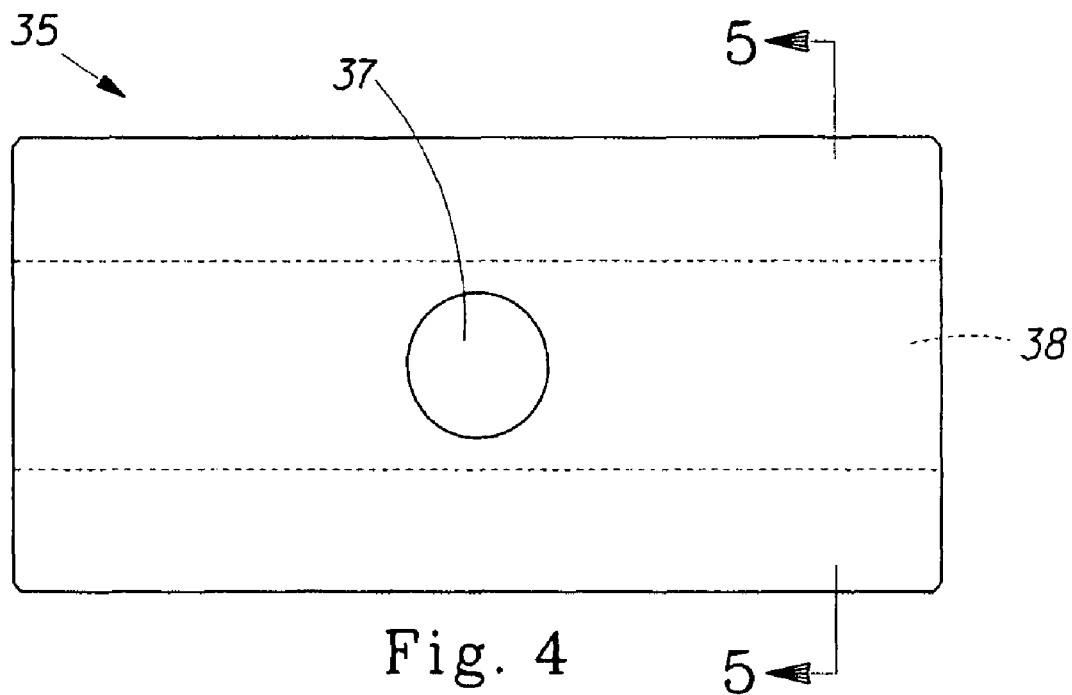
FIG. 4 is a side view of an embodiment of a measuring device of the present invention.
Figure 5:
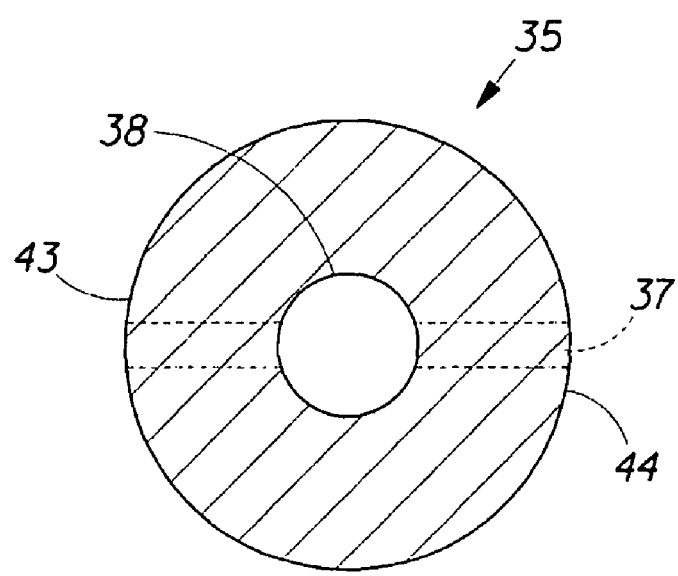
FIG. 5 is a cross-sectional view of section 5-5 of FIG. 4.

FIG. 3 is a side view of the measuring device 35 of FIG. 2. As mentioned above, and shown in FIG. 3 the attachment section 37 may be in the form of a notch or slot, that begins on one surface of the measuring device 35 and descends into the measuring device 35 to a depth "d". The depth of the attachment section 37 as measured from the surface of the measuring device 35 from which the attachment section 37 begins, is short of reaching the opposing surface of the measuring device 35. The attachment section 37 bisects the longitudinal passage 38 of the measuring device 35. The attachment section's 37 lowest point as measured from the surface of the measuring device 35 where the attachment section 37 begins, exposes the inside surface 45 of the longitudinal passage 38 to the outside environment. In certain embodiments, the distance between the first side 37a and the second side 37b of the attachment section 37 varies along the depth "d" of the attachment section 37. In certain embodiments, the measuring device 35 encloses the attachment section 37 along the attachment section's 37 width, such that the attachment section 37 is an enclosed channel traversing one side 43 of the measuring device 35 to the other side 44, as shown in FIGS. 4 and 5.

Referring back to FIG. 3, in certain embodiments the part of the first side 37a and second side 37b of the attachment section 37 that contacts the surface of the measuring device 35 may be angled (beveled). The beveling of the first side 37a and second side 37b, aids the withdrawal means 24 enter the attachment section 37. As shown in FIG. 3 in certain embodiments the angle "T" as measured from the surface of the first side 37a or second side 37b of the attachment section 37 ranges from about 5 degrees to about 80 degrees, and in certain other embodiments from about 15 degrees to about 60 degrees. In certain embodiments, the deepest portion of the attachment section 37 may contain a contact area 39 that is wider than the distance between the first side 37a and second side 37b of the attachment section 37. The contact area 39 helps facilitate the movement of the measuring device 35 along the length of the withdrawal means 24, in that the contact area 39 is sized to fit loosely around the withdrawal means 24.

Figure 6:
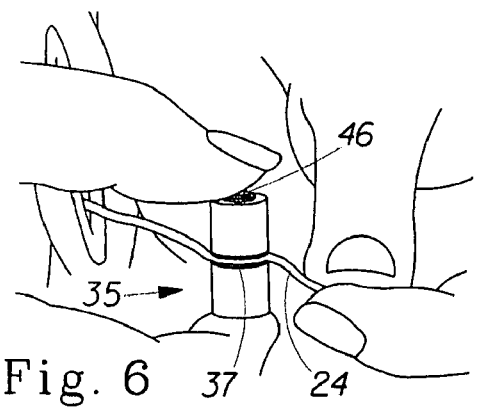
FIG. 6 is a perspective view of an embodiment of the present invention.
Figure 7:
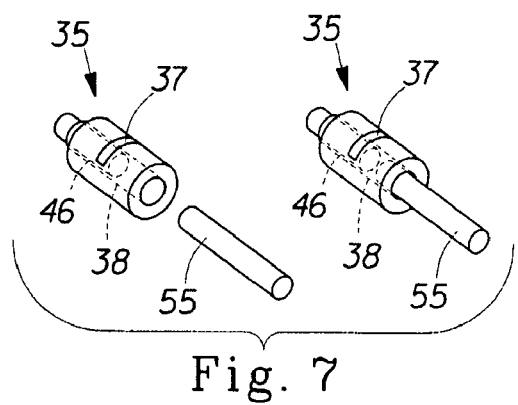
FIG. 7 is a perspective view of an embodiment of a measuring device of the present invention.

Referring to FIG. 6 the measuring device 35 may be slidably attached to the withdrawal means 24 using the attachment section 37, and then moved along the length of the withdrawal means 24 towards the vaginal opening. However, in certain embodiments as shown in FIG. 7, the fastener 46 may be in a position within the longitudinal passage 38, where the fastener 46 partially or completely blocks the attachment section 37. This blockage caused by the positioning of the fastener 46 within the longitudinal passage 38, may prevent the measuring device 35 from being slidably attached to the withdrawal means 24. Therefore, as shown in FIG. 7 if the fastener 46 is blocking the attachment section 37 an evacuation rod 55 may be moved into the opening of the longitudinal passage 38 that is opposite the fastener 46. Pressure is then applied to the evacuation rod 55, to move the fastener 46 away from the attachment section 37. After the fastener 46, has been moved away, the measuring device 35 can be slidably attached to the withdrawal means 24 using the attachment section 37.

Figure 8:
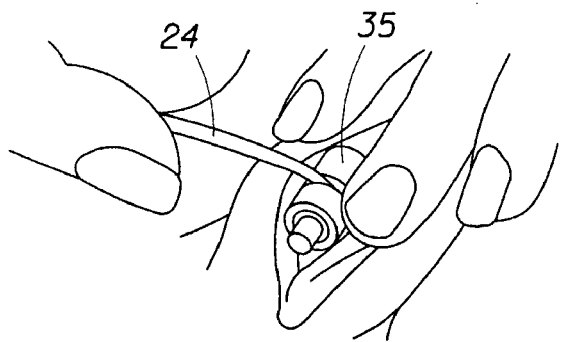
FIG. 8 is a perspective view of an embodiment of the present invention.
Figure 9:
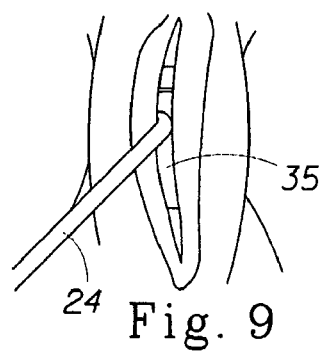
FIG. 9 is a perspective view of an embodiment of the present invention.
Figure 10:
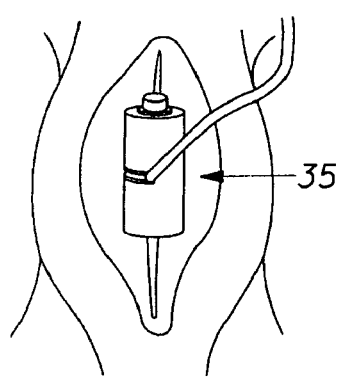
FIG. 10 is a perspective view of an embodiment of the present invention.

FIGS. 8 and 9 show the measuring device 35 being moved along the length of the withdrawal means 24 to the vaginal opening. In certain other embodiments as shown in FIG. 10, the measuring device 35 may be moved along the length of the withdrawal means 24 to the outer portion of the labia, which in some users may be the labia minora, and in other users the labia majora. Wherein the outer portion of the labia, is the portion of the labia that the measuring device 35 would contact first, while being moved along the withdrawal means 24 towards the vaginal opening.

Figure 11:
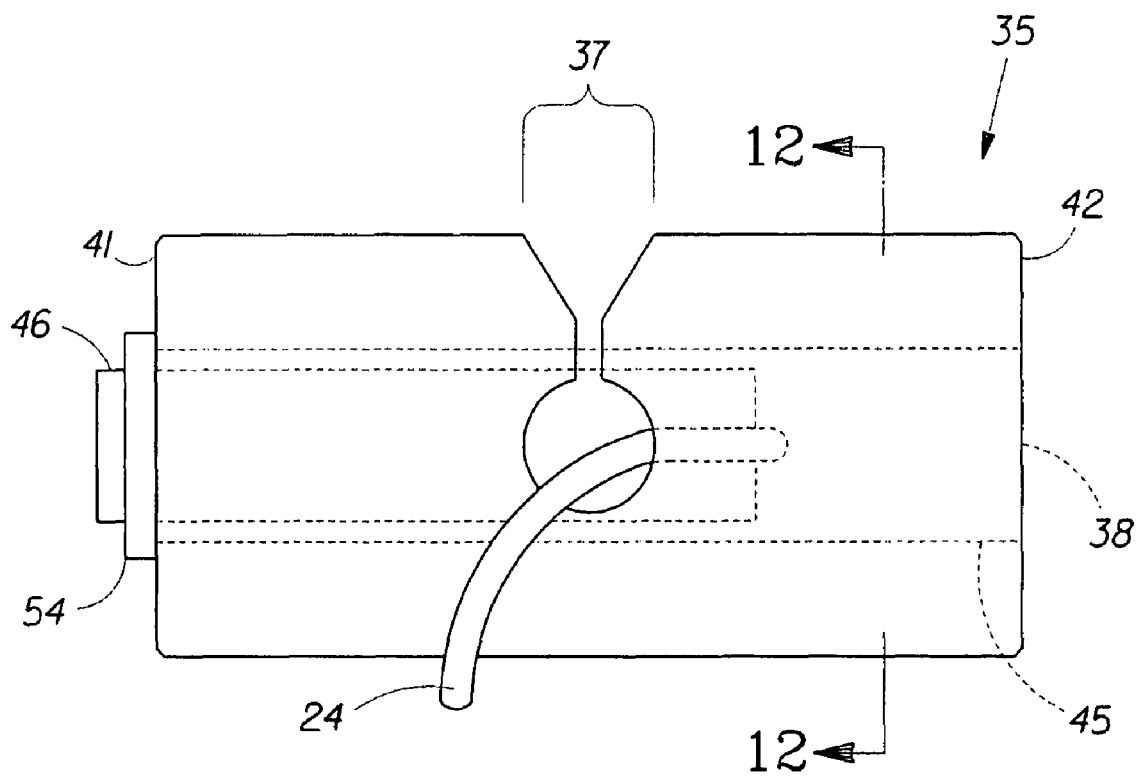
FIG. 11 is a side view of an embodiment of a measuring device of the present invention.
Figure 12:
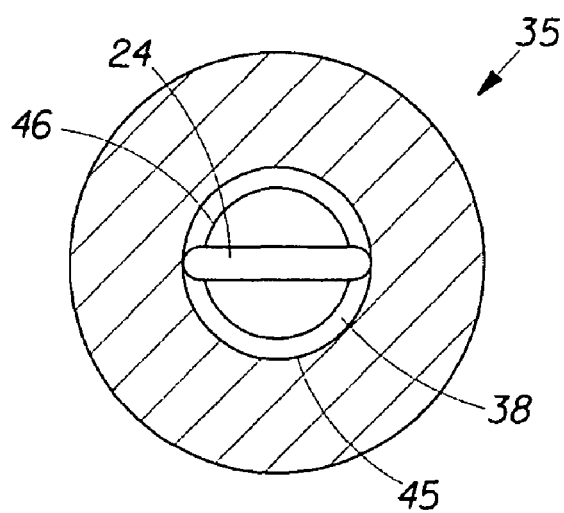
FIG. 12 is a cross-sectional view of section 12-12 of FIG. 11.

When the measuring device 35 is at the desired location on the withdrawal means 24, the measuring device 35 may be fixedly secured to the withdrawal means 24, such as by mechanically or frictionally fixedly securing the measuring device 35. As used herein, the term fixedly secured, refers to when the measuring device 35 may not move along the length of the withdrawal means 24 absent the application of force. In certain embodiments, the force applied is in the range of about 0.1 N to about 10 N, and wherein the range between about 0.1 N and about 10 N is measured in increments of 0.1 N. In certain other embodiments, the force applied is in the range of about 1 N to about 5 N, and wherein the range between about 1 N and about 5 N is measured in increments of 0.1 N. The fastener 46 may mechanically fixedly secure the measuring device 35 to the withdrawal means 24, by pressing the withdrawal means 24 between the sides of the fastener 46 and the surface 45 of the longitudinal passage 38, as shown in FIGS. 11 and 12. As shown in FIG. 11 a fastener 46 can be at least partially positioned within the longitudinal passage 38 at the first end 41 or second end 42 of the measuring device 35. The fastener 46 is dimensioned to move within the longitudinal passage 38. In certain embodiments, when the measuring device 35 is at the vaginal opening or the outer portion of the labia, the fastener 46 is moved within the longitudinal passage 38 past the attachment section 37 and into contact with the withdrawal means 24. In certain other embodiments, the measuring device 35 may be frictionally fixedly secured to the withdrawal means 24, through the use of the attachment section 37. The sides 37a, 37b of the attachment section 37 compress the withdrawal means 24. The compression creates a frictional force between the withdrawal means 24 and the sides 37a, 37b of the attachment section 37, which frictionally fixedly secures the measuring device 35 to the withdrawal means 24.

Referring to FIG. 11, in certain embodiments, a protective ring 54 may be fitted around the fastener 46 to hold the fastener 46 in place within the longitudinal passage 38. The protective ring 54 may be produced from an elastic or stretchable material such as rubber. This allows the protective ring 54 to fit securely around the fastener 46. After the protective ring 54 is fitted around the fastener 46, the maximum diameter of the protective ring 54 is greater than the maximum diameter of the longitudinal passage 38. The greater diameter of the protective ring 54 prevents the fastener 46 from moving within the longitudinal passage 38 absent the application of pressure to the fastener 46.

Figure 13:
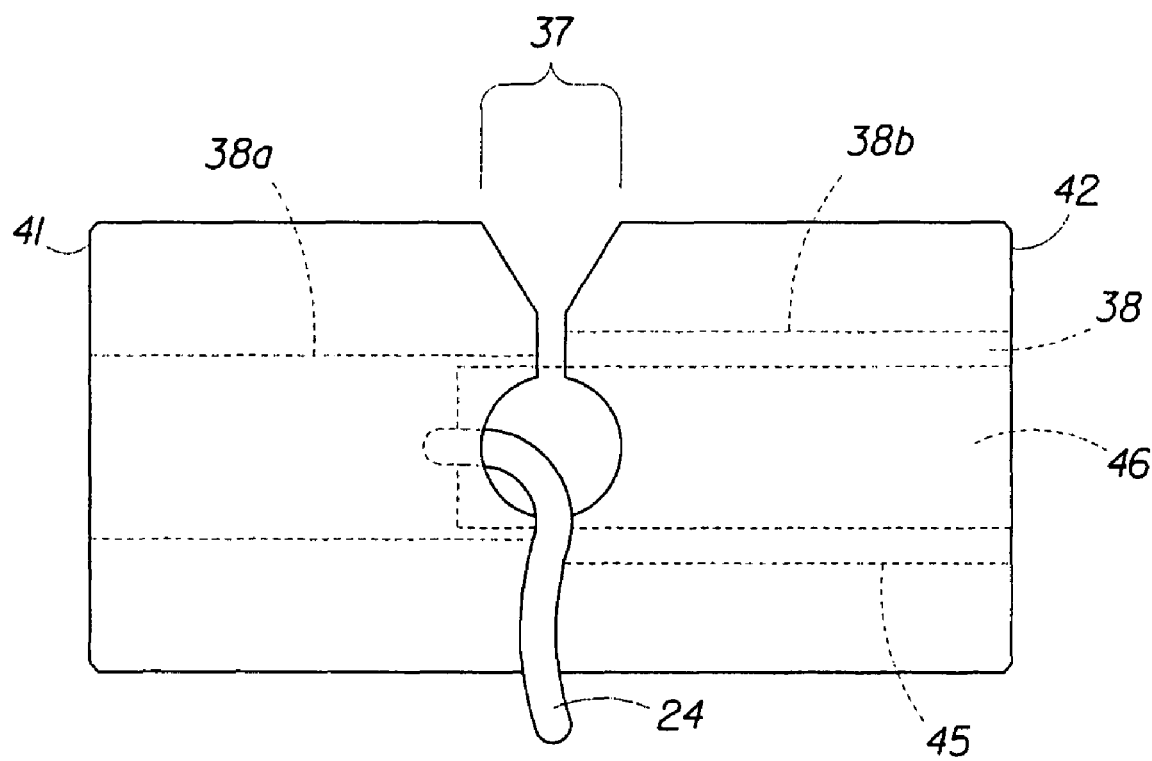
FIG. 13 is a side view of an embodiment of a measuring device of the present invention.

In certain embodiments as shown in FIG. 13, the longitudinal passage 38 may have two or more sections 38a, 38b differentiated by diameter along the longitudinal length of the measuring device 35. For example, the longitudinal passage 38 may have a narrow section 38a that extends from the first end 41 of the measuring device 35 to the attachment section 37. This narrow section 38a is narrower in diameter, in comparison to the diameter of a wider section 38b of the longitudinal passage 38, which extends from the attachment section 37 to the second end 42. The diameter of the wider section 38b of the longitudinal passage 38 allows the fastener 46 to move within the longitudinal passage 38. The diameter of the narrower section 38a, is sized to allow the fastener 46 to secure the measuring device 35 to the withdrawal means 24, by pressing the withdrawal means 24 between the sides of the fastener 46 and the surface 45 of the longitudinal passage 38.

Figure 14:
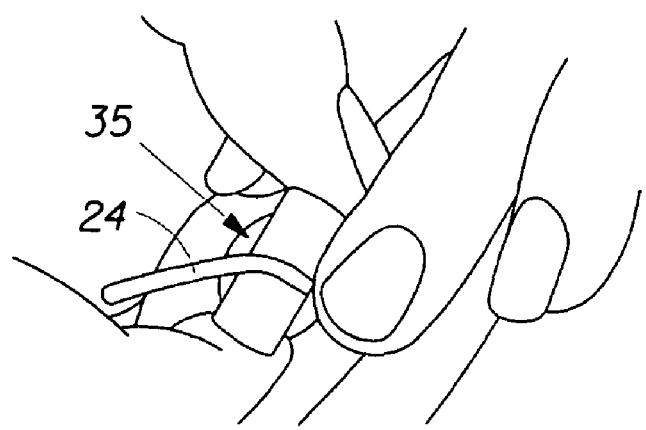
FIG. 14 is a perspective view of an embodiment of the present invention.
Figure 15:
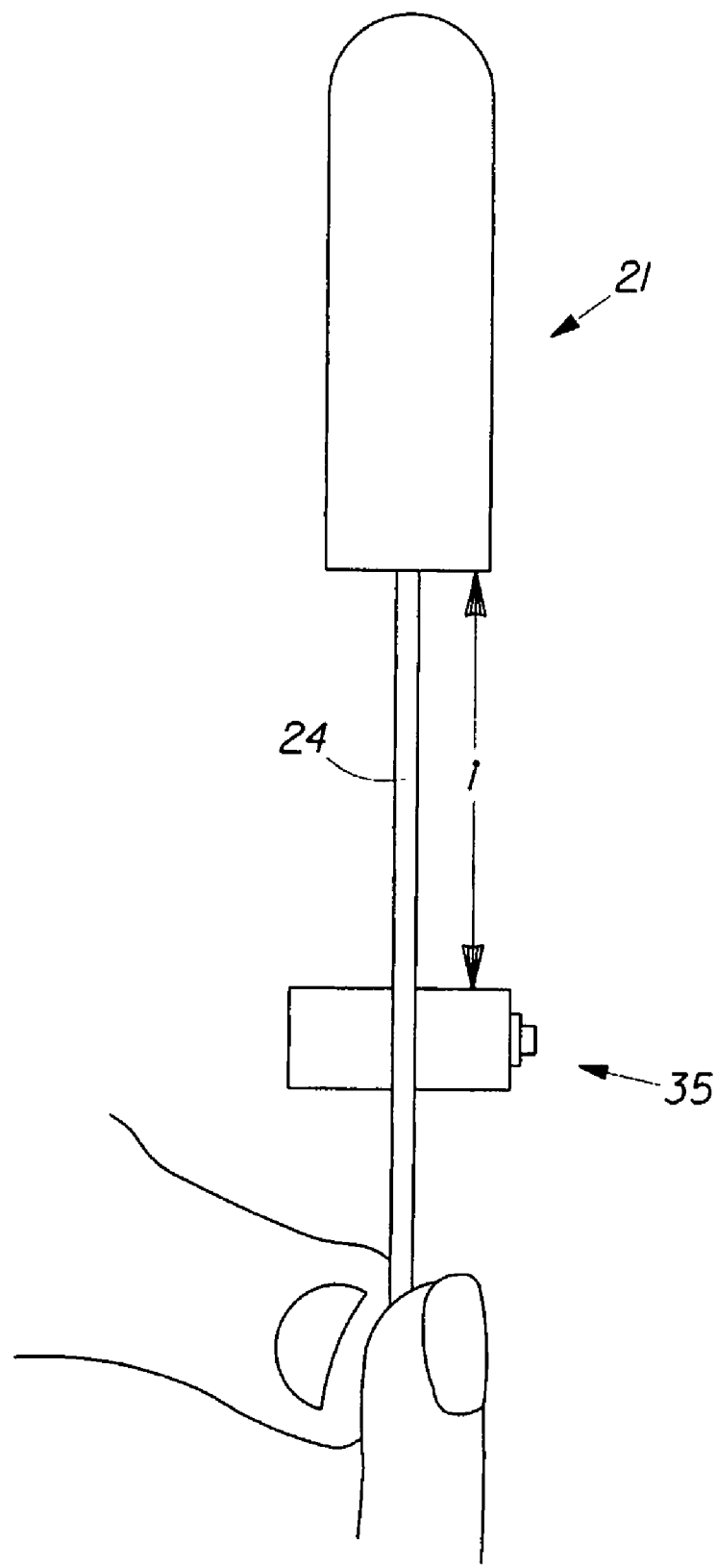
FIG. 15 is a perspective view of an embodiment of a tampon and measuring device of the present invention.

As shown in FIG. 14, the tampon 21 is then removed from the vaginal cavity. This may be done by applying a sufficient amount of pressure to the withdrawal means 24 and/or measuring device 35. In certain embodiments, the tampon 21 is removed from the vaginal cavity, without moving the measuring device 35 along the length of the withdrawal means 24. As shown in FIG. 15, in certain embodiments to determine the insertion distance "i" of the tampon, the length of the withdrawal means 24 between the withdrawal end 23 of the tampon 21 and the surface of the measuring device 35 closest to the withdrawal end 23 of the tampon 21 is measured.

Figure 16:
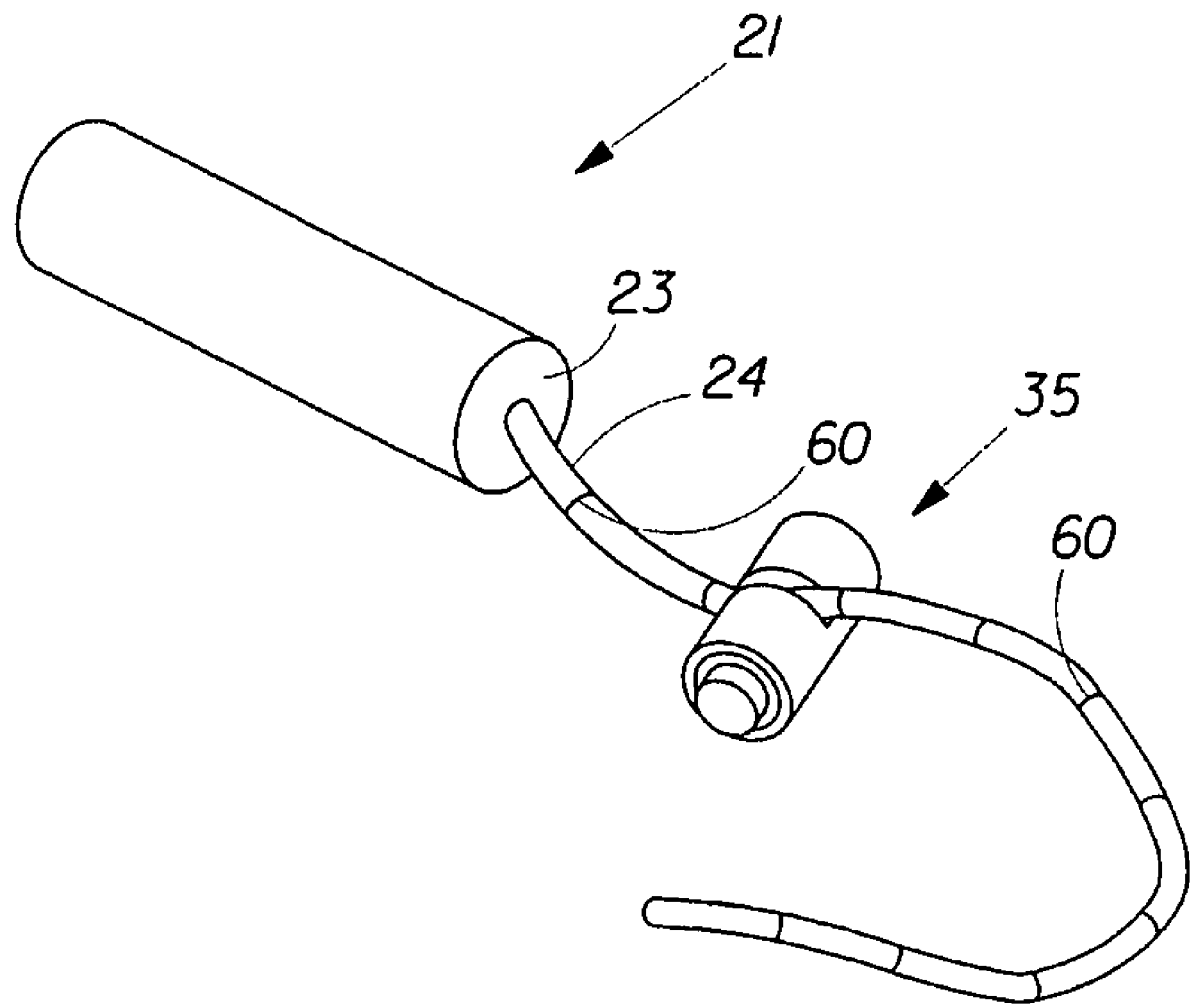
FIG. 16 is a perspective view of an embodiment of a tampon and measuring device of the present invention.

In certain embodiments, as shown in FIG. 16, an intravaginal article such as a tampon 21 may be provided, which comprises a withdrawal means 24 having indicators 60. The indicators 60 may be located on any portion of the withdrawal means 24. The indicators 60 can be in any form that communicates to a user the position of a measuring device 35 on the withdrawal means 24. For example, the indicators 60 could be in the form of hash marks, pictures, letters, numbers, colors, symbols, or combinations thereof. The indicators can be made by any method known by one of ordinary skill in the art such as by printing, weaving, embossing, transferring, stamping, or combinations thereof.

In certain embodiments before inserting the tampon, a user slidably attaches a measuring device 35 to the withdrawal means 24 of the tampon 21. The user then positions the measuring device 35 to an indicator 60 on the withdrawal means 24 of the tampon 21, and fixedly secures the measuring device 35 to the withdrawal means 24, as described previously for FIGS. 7 and 8. This allows a user to control the insertion distance of the tampon 21 within the vaginal cavity. The user then inserts the tampon 21 into the vaginal cavity. The user would stop inserting the tampon 21, once the measuring device came into contact with the vaginal opening or outer portion of the labia.

Based upon the performance of the tampon 21, the user may adjust the measuring device 35 along the length of the withdrawal means 24 using the indicators 60. For example, if greater insertion distance is desired the measuring device 35 may be moved to an indicator 60 farther away from the withdrawal end 23 of the tampon 21, than where the measuring device 35 was previously fixedly secured on the withdrawal means 24. If less insertion distance is desired, the measuring device 35 may be moved to an indicator 60 closer to the withdrawal end 23 of the tampon 21, than where the measuring device 35 was previously fixedly secured on the withdrawal means 24. Additionally, if the insertion distance of the tampon 21 did provide acceptable performance the user may note the indicator 60 on the withdrawal means 24 where the measuring device 35 was located. This allows the user to attach a measuring device 35 to an indicator 60 in the same position on another tampon 21 to reproduce the same insertion distance. After the tampon 21 is inserted the measuring device 35 may be removed from the withdrawal means 24 by moving the fastener 46 away from the attachment section 37 to release the withdrawal means 24.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for determining the insertion distance of a tampon within a vaginal cavity comprising the steps of:
    (a) providing a tampon wherein said tampon includes a withdrawal end and a withdrawal means;
    (b) inserting said tampon into a vaginal cavity;
    (c) providing a measuring device having an attachment section;
    (d) slidably attaching said attachment section of said measuring device to said withdrawal means by contacting said attachment section with said withdrawal means;
    (e) fixedly securing said measuring device to said withdrawal means;
    (f) removing said tampon from said vaginal cavity;
    (g) measuring insertion distance between a portion of said tampon and a portion of said measuring device.

2. The method of claim 1 wherein said measuring device is moved along said withdrawal means after being slidably attached to said withdrawal means.

3. The method of claim 1 wherein a fastener is used to fixedly secure said measuring device to said withdrawal means.

4. The method of claim 3 wherein the measuring device is detached from the withdrawal means by using an evacuation rod to move the fastener.

5. The method of claim 1 wherein said measuring device is fixedly secured to said withdrawal means at the vaginal opening or outer portion of the labia.

6. The method of claim 1 wherein the measuring of the insertion distance is between said withdrawal end of said tampon and the surface of said measuring device closest to said withdrawal end of said tampon.

7. A method for controlling the insertion distance of a tampon within a vaginal cavity comprising the steps of:
    (a) providing a tampon wherein said tampon includes a withdrawal means;
    (b) providing a measuring device having an attachment section;
    (c) slidably attaching said attachment section of said measuring device to said withdrawal means by contacting said attachment section with said withdrawal means;
    (d) fixedly securing said measuring device to said withdrawal means;
    (e) inserting said tampon into a vaginal cavity;
    (f) detaching said measuring device from said withdrawal means.

8. The method of claim 7 wherein said withdrawal means of said tampon includes at least one indicator.

9. The method of claim 8 wherein said measuring device is positioned to at least one indicator on said withdrawal means of said tampon.

10. The method of claim 7 wherein a fastener is used to fixedly secure said measuring device to said withdrawal means.

11. A tampon comprising:
    an absorbent member having a withdrawal end; and
    a withdrawal means attached to said absorbent member and extending beyond at least said withdrawal end, wherein a measuring device comprising an attachment section is slidably attached to said withdrawal means by said attachment section and can be fixedly secured to said withdrawal means.

12. The tampon of claim 11 wherein said measuring device is comprised of a substantially non-absorbent material that is at least one of wood, glass, metal, plastic, or combinations thereof.

13. The tampon of claim 11 wherein said measuring device includes at least one of a longitudinal passage, a fastener, an attachment section or combinations thereof.

14. The tampon of claim 13 wherein said longitudinal passage comprises two or more sections differentiated by diameter.

15. The tampon of claim 13 wherein a protective ring fits around said fastener.

16. The tampon of claim 11 wherein said withdrawal means includes at least one indicator.

17. The tampon of claim 16 wherein said indicator is at least one of a hash mark, picture, letter, number, color, symbol, or combinations thereof.

* * * * *